United States Patent
Yoshihara et al.

(12) 
(10) Patent No.: US 6,258,361 B1
(45) Date of Patent: Jul. 10, 2001

(54) AGENT FOR RECOVERING HEMATOPOIETIC FUNCTION AND PROCESSED FOOD BOTH CONTAINING TREATED PRODUCT OF PEANUT SEED COATS

(75) Inventors: Akio Yoshihara, 3-3-35, Kashiwacho, Shiki-shi, Saitama 353-0007 (JP); Nobuo Yahagi, Yamagata (JP); Shinji Fushiya; Fumihide Takano, both of Miyagi (JP); Hiroshi Hojo, Kanagawa (JP)

(73) Assignees: Akio Yoshihara; Manami Yahagi, both of (JP)

( * ) Notice: Subject to any disclaimer, the term of this patent is extended or adjusted under 35 U.S.C. 154(b) by 0 days.

(21) Appl. No.: 09/496,796

(22) Filed: Feb. 2, 2000

Related U.S. Application Data

(62) Division of application No. 09/284,915, filed on Apr. 21, 1999, now abandoned.

(30) Foreign Application Priority Data

Oct. 21, 1996 (JP) .................................................. 8-278309

(51) Int. Cl.[7] ........................ A61K 35/78; C07K 14/415; C12N 5/04

(52) U.S. Cl. ..................... 424/195.11; 435/410; 530/370; 800/298; 800/FOR 101; 426/655; 554/9

(58) Field of Search .......................... 424/195.1; 435/410; 530/370; 800/298, FOR 101; 426/655; 554/9

(56) References Cited

U.S. PATENT DOCUMENTS 4,323,648  4/1982  Tanzawa et al. ..................... 435/125

FOREIGN PATENT DOCUMENTS

| 48-10273 | 8/1973 | (JP) . | |
| 54-5053 | 1/1979 | (JP) | ................. A23L/1/36 |
| 57-206391 | 12/1982 | (JP) | ................. C12P/1/00 |
| 01165356 | 6/1989 | (JP) | ................. A23L/1/36 |
| 03273098 | 12/1991 | (JP) | ................. C11B/5/00 |
| 5-246816A | 9/1993 | (JP) | ................. A01N/65/00 |
| 07289197 | 11/1995 | (JP) | ................. A23L/1/229 |
| WO 94/16715 | 8/1994 | (WO) | ............................ A61K/35/12 |

Primary Examiner—Phuong T. Bui
(74) Attorney, Agent, or Firm—Pennie & Edmonds LLP

(57) ABSTRACT

The invention relates to a method for recovering hematopoietic function in a patient. The method includes administering orally to the patient an amount of a peanut seed coat-substance which exhibits bone marrow cell-proliferating activity and which is soluble in either water or ethanol, effective to recover hematopoietic function in the patient.

2 Claims, 2 Drawing Sheets

AGENT FOR RECOVERING HEMATOPOIETIC FUNCTION AND PROCESSED FOOD BOTH CONTAINING TREATED PRODUCT OF PEANUT SEED COATS

This is a division of application Ser. No. 09/284,915, filed Apr. 21, 1999, now abandoned.

DESCRIPTION

Technical Field

The present invention relates to an agent for recovering hematopoietic function and a processed food both containing a treated product of peanut seed coats.

Background Art

Antibiotic-type carcinostatics used in chemotherapy for cancer damage the function of bone marrow when administered for a long time, causing hematopoietic dysfunctions (represented by thrombocytopenia) and leukopenia. Among these side effects, the inhibition of lymphocyte functions associated with leukopenia causes remarkable decrease in natural curing ability in humans and infectious diseases in them. Thus, this side effect is a big obstacle to recovery from diseases.

In order to alleviate those side effects occurring in chemotherapy for cancer, recombinant formulations of cytokine genes which activate lymphocyte functions, such as human granulocyte colony-stimulating factor (rhG-CSF), human granulocyte-macrophage colony-stimulating factor (rhGM-CSF) and human macrophage colony-stimulating factor (rhM-CSF), are applied. However, since these medicines are protein formulations prepared by recombinant DNA technology, their cost per day is rather high and yet there are limitations in the term of use and in the administration method (intravenous injection). Therefore, development of effective medicines which are cheap and capable of oral administration is desired.

DISCLOSURE OF THE INVENTION

It is an object of the present invention to provide an agent for recovering hematopoietic function and a processed food both comprising a physiologically active substance which is derived from a natural product and capable of oral administration.

As a result of extensive search for a physiologically active substance having bone marrow cell-proliferating activity which occurs in the natural world and does not cause side effects, the present inventors have found that an extract from peanut seed coats and a treated product of the extract have an effect of proliferating bone marrow cells. Further, it was found that the extract and treated extract exhibit the above-mentioned effect even when administered orally and, thus, they are useful as an agent for recovering hematopoietic function and as a processed food. Thus, the present invention has been achieved.

The present invention includes the following inventions.
(1) An agent for recovering hematopoietic function comprising as an active ingredient a peanut seed coat-derived substance exhibiting bone marrow cell-proliferating activity or a culture obtained by culturing a nonpathogenic fungus in a medium containing peanut seed coats or a treated product of the culture.
(2) An agent for recovering hematopoietic function comprising as an active ingredient an extract from peanut seed coats or a treated product of the extract.
(3) A processed food comprising a peanut seed coat-derived substance exhibiting bone marrow cell-proliferating activity or a culture obtained by culturing a nonpathogenic fungus in a medium containing peanut seed coats or a treated product of the culture.
(4) A processed food comprising an extract from peanut seed coats or a treated product of the extract.

The fruit of peanut has a solid pericarp. Usually, there are two seeds present inside the pericarp. These seeds are covered with seed coats. In the present invention, these seed coats are used.

In the present invention, peanut seed coats are used as an extract or a treated extract, or as a culture obtained by culturing a nonpathogenic fungus in a medium containing peanut seed coats or a treated product of the culture.

In the present invention, the "peanut seed coat-derived substance exhibiting bone marrow cell-proliferating activity" may be any substance as long as it is obtained from peanut seed coat and has activity to proliferate bone marrow cells. For example, an extract from peanut seed coats or the extract which has been given at least one of such treatments as separation, purification, isolation, heating and alkali treatment and which retains activity to proliferate bone marrow cells may be given.

As an extraction solvent, water; alcohols such as methanol, ethanol, propanol, butanol; ethers such as ethyl ether, dioxane; ketones such as acetone; or the like may be used. When an extract is used as a dry material after removal of the solvent, any of the above-mentioned solvents may be used alone or in combination. When an extract is used in a state of solution dissolved in the solvent, a solvent harmless to human body must be used. In this case, it is preferable to use water, ethanol or a mixture of water and ethanol.

In the extraction, peanut seed coats may be used without any treatment. Alternatively, they may be crushed or powdered to give greater contact with the solvent.

A waste water generated in the process of separating peanut seed coats from peanut seeds by washing them with water and then purified or dried if necessary may be used as an extract. However, it is preferable to extract peanut seed coats with a solvent in an amount of 5 to 25 liters per kg of the coats.

Extraction temperature ranges preferably from room temperature to the boiling point of the solvent under ambient pressure. Extraction period is preferably one day though it varies depending on the extraction temperature.

The thus obtained extract as it is may be used as a component of the agent for recovering hematopoietic function or the processed food of the invention. Alternatively, the extract may be treated by various means of purification such as ion exchange chromatography, gel filtration chromatography, dialysis, etc. to obtain active fractions using bone marrow cell-proliferating activity as an indicator. Then, such a treated extract with enhanced activity may be used in the invention.

In the present invention, instead of the above-described extract or treated extract, a culture obtained by culturing a nonpathogenic fungus in a medium containing peanut seed coats or a treated product of the culture may be used. The culture or treated culture is especially preferable for use in various processed foods including health food.

The nonpathogenic fungus used in the invention is not particularly limited. For example, basidiomycetes such as polypores, *Tricholoma matsutake* (matsutake fungus), *Lentinus endodes* (shiitake fungus), *Grifola frondosa*; and ascomycetes such as *Onygena corvina* and fungi belonging to the genus Cordyceps may be enumerated.

The above-described culture obtained by culturing a nonpathogenic fungus in a medium containing peanut seed coats may be used as it is as a component of the agent for recovering hematopoietic function or the processed food of the invention. Alternatively, the culture may be given a physicochemical treatment such as such photo treatment or pH adjustment; or a biochemical treatment such as fermentation and used as a treated culture.

The agent of the invention for recovering hematopoietic function can be formulated into pharmaceutical preparations by using an extract from peanut seed coats or a treated product of the extract, or a culture obtained by culturing a nonpathogenic fungus in a medium containing peanut seed coats or a treated product of the culture alone or in combination with a pharmaceutical carrier. The dosage form is not particularly limited and may be appropriately selected according to the route and method of administration. Generally, the agent of the invention is used as oral agents such as tablets, capsules, granules, fine granules or powder.

The dosage of the agent of the invention for recovering hematopoietic function varies depending on the age, weight and degree of the disease of a patient. In oral administration, the dosage ranges usually from 100 to 500 mg per day as dry powder of peanut seed coat extract. Usually, the number of administration is once to three times a day in oral administration.

In the present invention, a culture obtained by culturing a nonpathogenic fungus in a medium containing peanut seed coats or a treated product of the culture is preferably used as a component of processed foods. The dosage in this case is usually 100 to 500 mg per day as the culture or treated culture. The number of administration is usually one to three times a day.

Such oral agents and processed foods are prepared by conventional methods using excipients starch, lactose, sucrose, mannitol, carboxymethylcellulose, corn starch, inorganic salts, etc.

In such oral agents and processed foods, binders, disintegrants, surfactants, lubricants, fluidity promoters, flavoring agents, coloring agents, perfumes and the like may also be used appropriately in addition to the abovementioned excipient.

As binders, crystalline cellulose, crystalline cellulose/carmellose sodium, methylcellulose, hydroxypropylcellulose, hydroxypropylcellulose with a low degree of substitution, hydroxypropylmethylcellulose 2208, hydroxypropylmethylcellulose 2906, hydroxypropylmethylcellulose 2910, hydroxypropylmethylcellulose phthalate 200731, hydroxypropylmethylcellulose phthalate 220824, hydroxypropylmethylcellulose acetate succinate, carmellose sodium, ethylcellulose, carboxymethylethylcellulose, hydroxyethylcellulose, wheat starch, rice starch, corn starch, potato starch, dextrin, gelatinized starch, partially gelatinized starch, hydroxypropylstarch, pullulan, polyvinylpyrrolidone K25, polyvinylpyrrolidone K30, aminoalkyl methacrylate copolymer E, aminoalkyl methacrylate copolymer RS, methacrylate copolymer L, methacrylate copolymer S, methacrylate copolymer LD, polyvinyl acetal diethyl aminoacetate, polyvinyl alcohol, acacia, powdered acacia, agar, gelatin, white shellac, tragacanth gum, purified sucrose, macrogol 200, macrogol 300 and macrogol 6000 may be enumerated, for example.

As disintegrants, crystalline cellulose, methylcellulose, hydroxypropylcellulose with a low degree of substitution, carmellose, carmellose calcium, carmellose sodium, crosscarmellose sodium, wheat starch, rice starch, corn starch, potato starch, partially gelatinized starch, hydroxypropyl starch, sodium carboxymethyl starch and tragacanth gum may be enumerated, for example.

As surfactants, soybean lecithin, sucrose fatty acid esters, polyoxyl stearate 40, polyoxyethylene hardened castor oil 100, polyoxyethylene hardened castor oil 40, polyoxyethylene hardened castor oil 50, polyoxyethylene hardened castor oil 60, polyoxyethylene[42] polyoxypropylene[67] glycol, polyoxyethylene[54] polyoxypropylene[39] glycol, polyoxyethylene[105] polyoxypropylene[5] glycol, polyoxyethylene[160] polyoxypropylene[80] glycol, polyoxyethylene[196] polyoxypropylene[67] glycol, sorbitan sesquioleate, sorbitan trioleate, sorbitan monostearate, sorbitan monopalmitate, sorbitan monolaurate, polysorbate 40, polysorbate 60, polysorbate 65, polysorbate 80, glycerol monostearate, sodium lauryl sulfate and lauromacrogol may be enumerated, for example.

As lubricants, wheat starch, rice starch, corn starch, stearic acid, calcium stearate, magnesium stearate, hydrous silicon dioxide, light anhydrous silicic acid, synthetic aluminium silicate, dry aluminium hydroxide gel, talc, magnesium alminate metasilicate, calcium hydrogenphosphate, anhydrous calcium hydrogenphosphate, sucrose fatty acid esters, waxes, hydrogenated vegetable oils and polyethylene glycol may be enumerated, for example.

As fluidity promoters, hydrous silicon dioxide, light anhydrous silicic acid, dry aluminium hydroxide gel, synthetic aluminium silicate and magnesium silicate may be enumerated, for example.

The agent for recovering hematopoietic function and the processed food of the invention may also be administered as a suspension, emulsion, syrup or elixir. These formulations may contain flavoring agents, aromatics and coloring agents.

Peanut seed coats which is a raw material for preparing the agent for recovering hematopoietic function and the processed food of the invention is served, together with peanut seeds, as food. Thus, the safety of this material has been established.

AHPE: cold immersion extract from peanut seed coats

AHPHE: hot water extract from peanut seed coats

AH seed extract: cold immersion extract from peanut seeds

Saline: cell proliferation when cells are cultured in saline alone

BEST MODES FOR CARRYING OUT THE INVENTION

The present invention will be described more specifically below with reference to the following Examples. However, the scope of the present invention is not limited to these Examples.

EXAMPLE 1

(1) Preparation of Extract from Peanut Seed Coats

Seeds of peanut (*Arachis hypogaea*) (Leguminosae) produced in China were dried for about one month, and then their seed coats were separated. Twenty-five grams of the dried seed coat was weighed accurately and placed in a 2 liter Erlenmeyer flask. One liter of purified water was added thereto and allowed standing at room temperature (22±3° C.) for 24 hours. The resultant mixture was filtered with a filter cotton, and the filtrate was freeze-dried to thereby obtain peanut seed coat extract powder (yield: 4.4484 g per 25 g of peanut seed coats). This powder is hygroscopic, reddish brown, fine powder without smell and with a bitter taste. This powder is readily soluble in both water and ethanol.

(2) Experiment on Bone Marrow Cell Proliferating Activity

Mouse bone marrow cells were used in this experiment. Briefly, C57BL/6 mice (specific pathogen free, female, 5–6 week old; purchased from SLC Japan) were slaughtered under excessive etherization. Two thigh bones were removed from each mouse aseptically. Subsequently, a 2.5 ml syringe (Terumo Corp.) provided with a 23 gauge needle (Terumo Corp.) was filled with α-MEM (commercial product of Gibco; containing 20% fetal bovine serum, 5% bovine serum albumin, 50 µM 2 mercaptoethanol) medium for culturing bone marrow cells. The upper edge of the thigh bone was pierced with the above-mentioned needle to thereby separate bone marrow cells. The resultant bone marrow cells were arranged to give a concentration of $5 \times 10^4$ cells/ml and added to 96-well culture plates (Becton Dickinson). To this cell culture fluid, the extract from peanut seed coats (obtained in (1) above; hereinafter referred to as the "cold immersion extract") which was diluted with saline to give a concentration of 25–200 µg/ml or saline alone as a control was added. Then, cells were cultured for 14 days.

Bone marrow cell-proliferation was judged by colorimetry using MTT (3-(4,5-dimethylthiazole-2-yl)-2,5-diphenyltetrazolium bromide) which is a common method for assaying cell proliferation ratios.

As positive controls for bone marrow cell proliferation effect, interleukin 3 (IL-3; WEHI3 mouse lymphoma culture supernatant) and interleukin 6 (IL-6; mouse recombinant formulation from Genzyme) of which proliferation effect on bone marrow cells had been confirmed were used.

Figure 1:
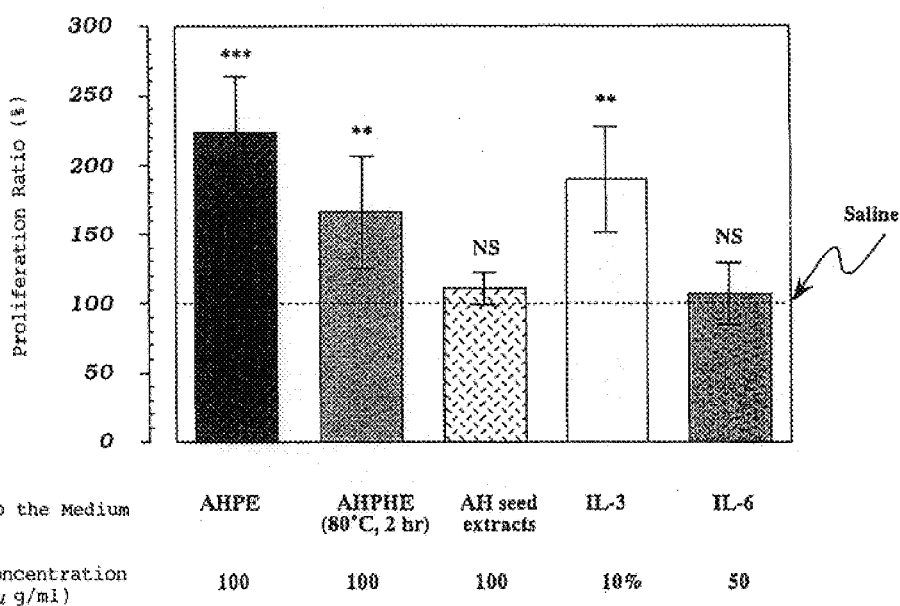
FIG. 1 shows the effect of extract from peanut seed coats on bone marrow cell-proliferating activity.

The results are shown in FIG. 1. In these data, the cell proliferation ratio when cultured by saline alone (see Saline in the Figure) was taken as 100%. Proliferation ratios (%) against this value were expressed in mean value ± standard deviation value. Marks "*" and "**" represent statistically (Student t test) significant difference against the result obtained by culturing with saline alone. These marks were given to those experimental results of significance levels less than 1% and less than 0.1%, respectively. Mark "NS" was given when the results exceeded the above-mentioned significance levels and no statistically significant difference was recognized.

Addition of the cold immersion extract from peanut seed coats exhibited bone marrow cell-proliferating activity 2 times greater (see the column "AHPE" in FIG. 1) than that obtained when saline alone (control) was added (proliferation ratio: 100%). This activity of the extract was found to be greater than the activity of IL-3 and IL-6, the cytokines used as positive controls (FIG. 1).

Figure 2:
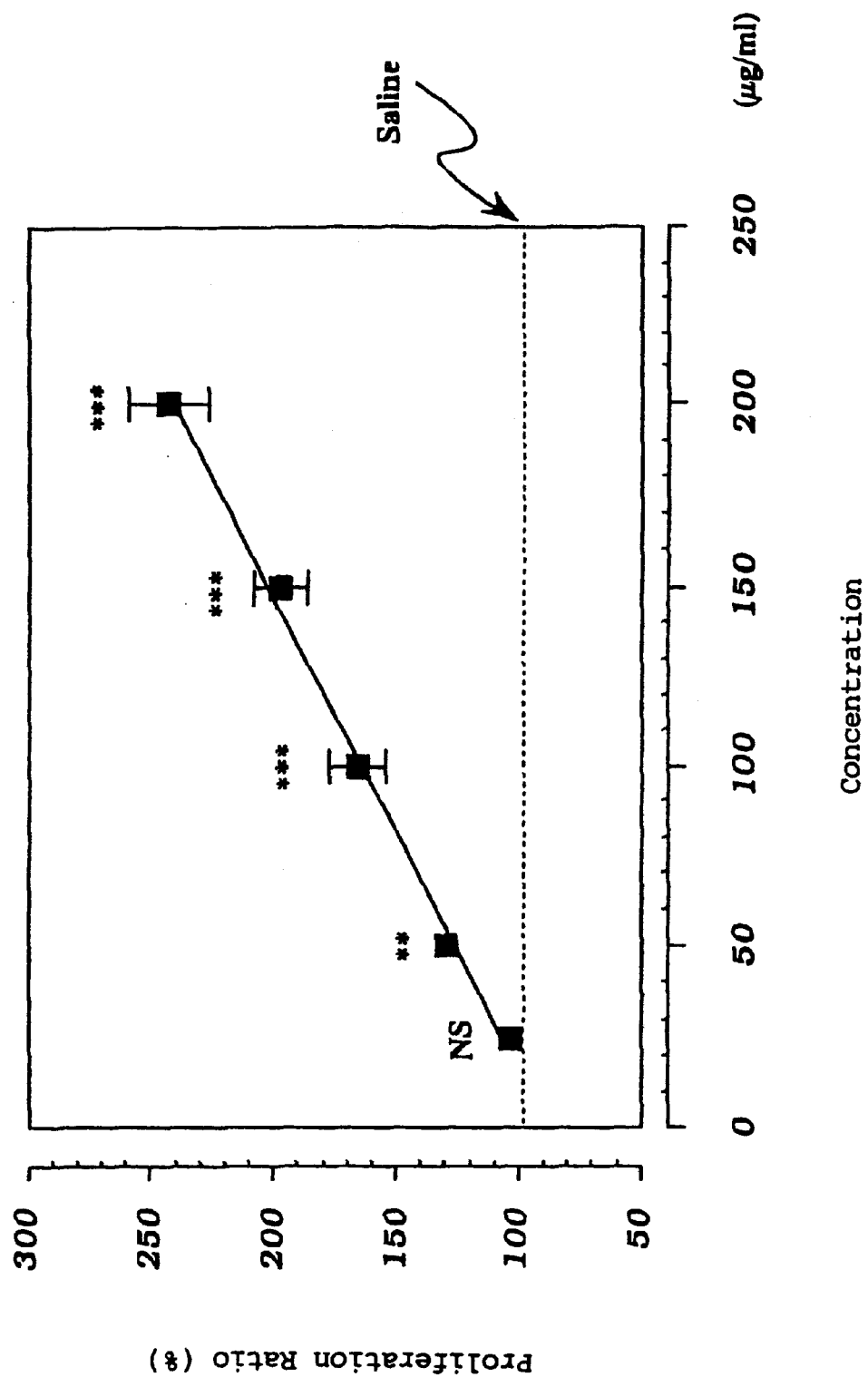
FIG. 2 shows the concentration dependency of the bone marrow cell-proliferating activity of extract from peanut seed coats.

The results of an experiment in which the concentration of the cold immersion extract was varied from 25 to 200 µg/ml are shown in FIG. 2. Concentration dependency was recognized in the activity of the cold immersion extract from peanut seed coats. At a concentration of 70 µg/ml or above, remarkable bone marrow cell-proliferating activity was recognized. Marks in FIG. 2 are the same as defined in FIG. 1.

It should be noted that no bone marrow cell-proliferating activity was recognized in extract from peanut seeds from which seed coats were removed (FIG. 1). Thus, it has become clear that this proliferating activity is the activity of peanut seed coats. Bone marrow cell-proliferating activity was also examined on extract powder which was obtained by extracting peanut seed coats with hot water of 80° C. for 2 hours to improve the extraction efficiency. As a result, it was found that the hot water extract had lower bone marrow cell-proliferating activity than the cold immersion extract. Therefore, it is considered that the cold immersion extract is more effective as an agent for recovering hematopoietic function.

(3) Human Clinical Data when the Cold Immersion Extract was Used

The number of platelets in the blood in a normal human is 200,000 to 350,000.

Case A: The cold immersion extract powder obtained in (1) above was administered orally at a dosage of 500 mg/day to a 40-year old male whose number of platelets decreased to 30,000 because of the side effects of a carcinostatic and whose life was endangered. As a result, the platelet number was recovered to 350,000 on day 4 of the administration.

Case B: The extract powder was administered at a dosage of 150 mg/day to a 12-year old boy with leukemia for 4 days. As a result, the number of platelets become normal and his fever went down.

Case C: The extract powder was administered orally at a dosage of 150 mg/day for 15 days to a 60-year old female whose number of platelets decreased to 70,000 because of the side effects of a carcinostatic. As a result, the platelet number was recovered to 200,000.

Case D: A 69-year old male having primary pancreatic cancer which had metastasized to the liver was diagnosed to have disseminated intravascular coagulation (DIC) syndrome on January 27. The number of platelets of this patient was 10,000. From the afternoon of January 29, administration of the cold immersion extract powder obtained in (1) above was started. Briefly, 500 mg of the extract powder was dissolved. One nineth (1/9) of this solution was administered orally 3 times a day. On January 30, the platelet number became 7,000; on February 1, the platelet number became 9,000; on February 3, the platelet number became 50,000; and on February 7, this number was recovered to 60,000.

In addition to the above cases, there are a number of clinically effective human cases. The extract powder was also effective for treating hematopoietic dysfunctions such as thrombocytopenia in purpura.

EXAMPLE 2

Peanut seed coats (1100 mg) were immersed in 100 ml of hot water (85° C.) for 1 min and 30 sec. Then, the resultant liquid with bloody red color was filtered, and the filtrate was filled in a bottle. The bottle was heated at 110° C. for 10 min to thereby degass the liquid in it. After the degassing, a stainless cap was put on the bottle, which was stoppered tightly. The liquid in the tightly stoppered bottle was dipped in hot water of 90° C. for 2 hours for sterilization. As a result of the heating operation, the liquid in the bottle became a clear drink presenting bloody red color.

EXAMPLE 3

Peanut seed coats (1500 mg) was decocted in 500 ml of water in an earthen teapot over a low fire so that a half of the water was evaporated in 30 min. The resultant bloody red liquid was filtered to obtain the filtrate as a dosage per day per human.

EXAMPLE 4

Peanut seed coats were immersed in hot water (85° C.) for 1 min and 30 sec. Then, the seed coats were removed from the liquid and washed with water until no bloody red color from the extract came out. The thus washed seed coats were dried completely with hot air of 80° C. To 200 g of the dried seed coats, 10 liters of water and 5 g of sodium hydrogencarbonate were added and reacted at 90° C. for 60 min under agitation. The filtrate was heated under refluxing for 60 min and then freeze-dried to thereby obtain powder which was about 0.371% of the dried seed coats.

The thus obtained powder can be used as it is as an active ingredient of the agent of the invention for recovering hematopoietic function, or it can be used as a raw material for preparing the processed food of the invention.

EXAMPLE 5

A sterilized medium was prepared by adding to peanut seed coats 0.1% vitamins and 0.1% minerals. To this medium, spores of a basidiomycete (e.g. polypore) or ascomycete (e.g. Cordyceps fungus) were inoculated and cultured. After the maturation of hyphae, fruit bodies were formed. The fruit bodies and aggregations of the fungus were dried and powdered.

The thus obtained powder can be used as it is as an active ingredient of the agent of the invention for recovering hematopoietic function, or it can be used as a raw material for preparing the processed food of the invention.

EXAMPLE 6

A sterilized medium was prepared by adding to peanut seed coats vitamins, minerals and saccharides. To this medium, spores of a basidiomycete (e.g. polypore) or ascomycete (e.g. Cordyceps fungus) were inoculated and cultured. After the maturation of hyphae, fruit bodies were formed. The fruit bodies and the entire medium were boiled in hot water of 90° C. for 120 min under agitation. The filtrate was heated under refluxing for another 60 min, and then freeze-dried to obtain powder.

The thus obtained powder can be used as it is as an active ingredient of the agent of the invention for recovering hematopoietic function, or it can be used as a raw material for preparing the processed food of the invention.

EXAMPLE 7

The freeze-dried powder obtained in Example 6 (400 mg) was filled in a 350 ml bottle and degassed. The bottle was stoppered tightly and finally sterilized to prepare a drink.

EXAMPLE 8

Peanut seed coats were placed in 99.9% ethanol at 18° C. in such a manner that the precipitated seed coats occupied 30% of the volume of the ethanol, and left stationary for 40 days. Then, the extract was freeze-dried to prepare powder.

The thus obtained powder can be used as it is as an active ingredient of the agent of the invention for recovering hematopoietic function, or it can be used as a raw material for preparing the processed food of the invention.

EXAMPLE 9

The powder obtained in Example 8 (10 g) was mixed with 490 g of corn starch and kneaded with addition of water. The resultant material was granulated through a screen of 1 mm×1 mm meshes and dried to prepare granules.

One gram of the thus obtained granules contains 20 mg of the powder obtained in Example 8. Five to 10 grams of these granules is administered 3 times a day according to the symptoms of a patient.

INDUSTRIAL APPLICABILITY

The agent of the invention for recovering hematopoietic function has an effect of recovering hematopoietic function such as increasing platelet-producing ability, is capable of oral administration and is prepared from a safe food as a raw material. Thus, according to the present invention, the field of clinical application of hematopoietic function recovering agent can be enlarged. The agent of the invention is especially effective when bone marrow function was decreased due to the use of carcinostatics or radio therapies or when disorders in platelet production are caused by hepatic diseases or blood diseases.

Further, the processed food of the invention also has an effect of recovering hematopoietic function such as increasing platelet-producing ability and is prepared from a safe food as a raw material. Thus, the processed food of the invention is widely applicable to various foods including health food.

What is claimed is:

1. A method for recovering hematopoietic function in a patient, the method comprising; administering orally to the patient a water immersion extract of peanut seed coats which exhibits bone marrow cell-proliferating activity in an amount effective to recover hematopoietic function in the patient.

2. The method according to claim 1, wherein the water immersion extract of peanut seed coats is a water extract obtained at room temperature.

* * * * *